United States Patent [19]

Prichard

[11] 4,255,338

[45] Mar. 10, 1981

[54] PROCESS FOR THE PREPARATION OF 2,5-DIHYDROFURAN

[75] Inventor: William W. Prichard, Hockessin, Del.

[73] Assignee: E. I. Du Pont de Nemours and Company, Wilmington, Del.

[21] Appl. No.: 84,631

[22] Filed: Oct. 12, 1979

Related U.S. Application Data

[62] Division of Ser. No. 13,236, Feb. 21, 1979.

[51] Int. Cl.$^3$ ............................................ C07D 307/28
[52] U.S. Cl. ............................... 260/346.11; 568/857; 568/861
[58] Field of Search .................... 260/346.11; 568/857, 568/861

[56] References Cited

U.S. PATENT DOCUMENTS

| 2,440,678 | 5/1948 | Ford et al. | 260/683.6 |
|---|---|---|---|
| 2,879,306 | 3/1959 | Hutchinson | 260/635 |
| 4,002,692 | 1/1977 | Mabuchi et al. | 260/617 R |
| 4,112,004 | 9/1978 | Mabuchi et al. | 568/861 |
| 4,123,616 | 10/1978 | Mabuchi et al. | 568/861 |

FOREIGN PATENT DOCUMENTS

| 2232699 | 1/1973 | Fed. Rep. of Germany . |
|---|---|---|
| 49-43908 | 4/1974 | Japan . |
| 50-96634 | 8/1975 | Japan . |
| 1018661 | 1/1966 | United Kingdom . |

OTHER PUBLICATIONS

Handy et al., J.A.C.S., vol. 80 (1958) pp. 5306–5308.

*Primary Examiner*—Richard Raymond

[57] ABSTRACT

A process for the hydrogenation of butadienepolyperoxide in a suitable solvent, e.g., tetrahydrofuran, at temperatures of 75°–110° C. and pressure above 2000 psia by contacting the butadienepolyperoxide and hydrogen in the presence of metallic silver. The process produces 1-butene-3,4-diol and 2-butene-1,4-diol.

2 Claims, No Drawings

PROCESS FOR THE PREPARATION OF 2,5-DIHYDROFURAN

This is a division of application Ser. No. 013,236, filed Feb. 21, 1979.

TECHNICAL FIELD

This invention relates to the preparation of diols from butadienepolyperoxide. More specifically, this invention relates to the preparation of butenediols from the hydrogenation of butadienepolyperoxide over a silver catalyst.

BACKGROUND ART

U.S. Pat. No. 2,879,306 discloses the hydrogenation of butadienepolyperoxide over palladium, nickel, rhodium, cobalt and platinum. A second stage hydrogenation over copper chromite, molybdenum sulfide and nickel is also disclosed. The resulting product is a mixture of 1,4-butanediol and 1,2-butanediol. The 1,2-butanediol is not used commercially and therefore is less valuable than the 1,4-butanediol.

Handy and Rothrock in J. American Chemical Society, 80, 5306 disclose the hydrogenation of butadienepolyperoxide in a silver-lined reactor over palladium followed by hydrogenation over ruthenium. The products were 2-hydroxybutanal, 1,2-butanediol and 1,4-butanediol.

British Pat. No. 1,018,661 discloses the hydrogenation of unsaturated organic hydroperoxides over modified palladium or platinum catalysts to give unsaturated alcohols. Modifiers disclosed include silver. An improvement in the amount of hydroperoxides reduced is shown with the modified catalysts.

Japanese Pat. Nos. 096634 and 087126 disclose the hydrogenation of butadeneperoxide polymer over Raney nickel to give 1,2- and 1,4-butanediol.

U.S. Pat. No. 4,002,692 discloses the hydrogenation of polymeric butadieneperoxide over a nickel catalyst to prepare 1,2- and 1,4-butanediol.

The reduction of butadienepolyperoxide to butanediols in the prior art gives maximum yields of the desired 1,4-butanediol of about 50% with a 20–30% yield of the commercially unattractive 1,2-butanediol. The reduction is carried out using a catalyst which rapidly becomes inactivated by contact with the peroxide and must be regenerated frequently. The reduction is very exothermic and is usually done stepwise under successively more severe conditions until reduction is complete.

The preparation of 1,4-butanediol is important not only for uses as solvents and monomers for the preparation of polyesters but also for use in the preparation of tetrahydrofuran.

The preparation of 1,4-butanediol by condensation of formaldehyde and acetylene to 2-butyne-1,4-diol followed by reduction to 1,4-butanediol is another process well known in the art and is a process that is practiced commercially. However, because of the escalating cost of acetylene, this process may rapidly become uneconomical.

Also described in the art is the oxidation of butane or benzene to maleic anhydride followed by reduction to butanediol or tetrahydrofuran.

DISCLOSURE OF THE INVENTION

Now a process has been found for the hydrogenation of butadienepolyperoxide to form butenediols.

Accordingly, the process of this invention is a process for the hydrogenation of butadienepolyperoxide which comprises hydrogenating a 1–20% by weight mixture of butadienepolyperoxide in a solvent which is not subject to hydrogenation in the presence of hydrogen and a catalyst comprising at least 0.1% by weight of metallic silver at a temperature of from 75°–110° C. and a pressure of at least 2000 psia to form a reaction product comprising 1-butene-3,4-diol and 2-butene-1,4-diol.

Hydrogenation of the 2-butene-1,4-diol yields 1,4-butanediol. Thus, 2-butene-1,4-diol can be converted to 1,4-butanediol by hydrogenation at 150°–200° C. using the same hydrogenation catalyst disclosed herein for the hydrogenation of the polyperoxide. However, 2-butene-1,4-diol may also be hydrogenated to 1,4-butanediol in the presence of a Raney nickel catalyst or other known hydrogenation catalysts according to procedures known in the art.

The 1-butene-3,4-diol can be converted to 2,5-dihydrofuran by treatment with a soluble mercury salt in a hydroxylic solvent as disclosed in the art, e.g., U.S. Pat. No. 3,812,158. 2,5-Dihydrofuran is useful in the preparation of tetrahydrofuran.

Butadienepolyperoxide can be prepared by converting butadiene thereto by any suitable oxidation process wherein a substantial portion of the butadiene is converted to the polyperoxide. Butadiene may be oxidized in a suitable solvent in the liquid phase in the presence of air or oxygen to form butadienepolyperoxide. The oxidation can be conducted in any suitable pressure reactor provided with means to thoroughly mix air or oxygen and the butadiene. Contact times for the oxidation are from 0.1–25, preferably 1–5 hours. Said oxidation is conducted in the temperature range of 35°–120° C. and at a partial pressure of oxygen of at least 20 psi. An initiator is preferably used to start the oxidation. Suitable initiators are organic peroxides or other precursors of free radicals such as azobisiosbutyronitrile. Oxidation promoters such as acetaldehyde, cobalt, linoleate and the like may be used.

The solvent for hydrogenating the butadienepolyperoxide is any solvent for butadienepolyperoxide that under the reaction conditions of hydrogenation disclosed herein is not hydrogenated and which does not cause decomposition of the polyperoxide. Representative examples include tetrahydrofuran, ethyl acetate, methyl acetate, 50–50 toluene-tetrahydrofuran, 50–50 benzene-tetrahydrofuran, similar esters and ethers and their combinations in the hydrocarbons. For economic reasons, the most suitable solvents are those which may also be used for the preparation of the polyperoxide, and methyl acetate is preferred.

The concentration of butadienepolyperoxide in the solvent may be up to 20% inclusive by weight. Concentrations of 1–20% by weight are generally used. Preferably the concentration of butadienepolyperoxide is 2.5–10% by weight in the solvent. Concentrations lower than 1% by weight, while operable, are uneconomic while concentrations higher than 20% may be dangerous. The hydrogenation is very exothermic and if reaction temperatures are allowed to rise above about 120° C., the polymer may decompose violently.

Butadienepolyperoxide hydrogenation temperatures from 75°–110° C. are generally used, with a preference for temperatures between 90°–105° C. Temperatures below 75° C., while operable, are uneconomical due to the slow reaction. Temperatures above 110° C. result in substantially more decomposition products thereby reducing the yield of diols.

The use of continuous flow equipment for the reaction is preferred and the rate of butadienepolyperoxide injection is a function of the peroxide concentration, of the weight of catalyst in the reactor, of the reaction temperature and the hydrogen pressure. At the higher permissible temperatures and pressures, the residence time in the reactor may be a few minutes while at the lower operable temperatures, a residence time of several hours may be necessary.

The pressure may generally range rather broadly. Best yields of diols are obtained at hydrogen pressures above 2000 psi. Pressures between 2000–5000 psi $H_2$ are preferred. However, higher pressures may be used.

The catalyst may be supported or unsupported silver metal. If unsupported, it may be prepared by reducing silver oxide with hydrogen or other reducing agents or by leaching out an alloy composition such as Ag-Zn with alkali to remove the Zn and leave a silver alloy skeleton with a high surface area. Supported catalysts may be prepared by reducing silver salts impregnated on a support by heating under hydrogen or by treating with a chemical reducing agent such as sodium borohydride. Suitable supports are silica, alumina, diatomaceous earth, carbon and titania. The most active silver catalysts are those prepared on high surface area supports.

The concentration of silver metal on the support may be 0.1% by weight or more. Generally, the silver metal concentration is from 0.1–10% by weight, preferably 1–10%. Supported catalysts are preferred because greater activity can be achieved per weight of silver present. Especially preferred are 1–10% Ag on high surface area silica gel catalyst.

The process of the present invention negates the disadvantages of the aforementioned prior art and commercial processes currently employed for the production of 1,4-butanediol. The subject process utilizes a starting material lower in cost than acetylene and formaldehyde (butadienepolyperoxide may be simply prepared by the oxidation of butadiene at 100° C. under low pressures). By reacting butadienepolyperoxide under critical temperature and pressure conditions in the presence of a silver catalyst which acts uniquely to allow cleavage of the —O—O— bonds and not the —C=C— bonds, the peroxide bonds are hydrogenolyzed without saturation of the carbon-to-carbon bonds to yield the unsaturated diols, 1-butene-3,4-diol and 2-butene-1,4-diol.

After solvent removal, the 1-butene-3,4-diol being lower boiling is readily separated from the 2-butene-1,4-diol. The 1-butene-3,4-diol separated from the reaction mix may be readily converted in good yields to 2,5-dihydrofuran. By converting the 1-butene-3,4-diol to a useful product (not possible with 1,2-butanediol) the yield of desirable products is increased. The 2,5-dihydrofuran may be hydrogenated directly to tetrahydrofuran or to a mixture of tetrahydrofuran and 1,4-butanediol. The 2-butene-1,4-diol remaining in the original reaction mixture is reacted further at temperatures of 150°–200° C. under a pressure of at least 2000 psi using the starting Ag catalyst to form 1,4-butanediol. If desired, the 2-butene-1,4-diol reaction product may be separately reacted using a Raney nickel catalyst to form the 1,4-butanediol. Thus, by utilizing the route of the present invention featuring the formation of the unsaturated diols as intermediates, an overall yield of over 75% of tetrahydrofuran plus 1,4-butanediol may be achieved. This high yield makes this process commercially advantageous. Another process advantage lies in the fact that the reduction of butadienepolyperoxide is very exothermic. By utilizing the process forming the unsaturated diols at lower reaction temperatures, as the intermediate step to the final formation of the desired end products (1,4-butanediol and tetrahydrofuran) and heat load is thereby split making the process easier to control.

The hydrogenation of the 2-butene-1,4-diol may be under the same conditions as indicated above for the butadienepolyperoxide hydrogenation except for the temperature which is in the range of 150°–200° C. However, any method known in the prior art may be used to hydrogenate the 2-butene-1,4-diol. For example, hydrogenation may be accomplished over a Raney nickel catalyst at from 50°–200° C. and from 30–5000 psi of hydrogen. Other known hydrogenation catalysts may be used. Under many conditions some of the other products in the reaction product, e.g. 4-hydroxybutyraldehyde, hydroxymethylvinylketone and 2-hydroxybutene-3-aldehyde, are also converted to diols during the hydrogenation.

The conversion of 1-butene-3,4-diol to 2,5-dihydrofuran by the process disclosed in U.S. Pat. No. 3,812,158 involves contacting the 1-butene-3,4-diol with soluble mercury salts such as $H_qSO_4$ in a hydroxylic solvent, e.g., water or butanol, which is neutral or acidic at a moderate temperature, e.g., 20°–110° C.

The conversion of 2,5-dihydrofuran to tetrahydrofuran is well known in the art.

EXAMPLES

The following examples further illustrate the process of the present invention. All percentages in the examples are by weight unless otherwise indicated.

Example 1

A Hastelloy C reactor of 5 ml volume was packed with 1.55 g of a 10% Ag on silica gel in fibrous form. The catalyst was prepared by impregnating the fibers with an ammoniacal silver nitrate solution, washing with dilute ammonium hydroxide and then with water and finally drying the product at 200° C. The dry catalyst was heated in the reactor at 250° C. for 54 hours under 2500 psi $H_2$ to reduce it. A solution containing 6.2% by weight butadienepolyperoxide in tetrahydrofuran and 1.147% by weight 1,6-hexanediol as a standard for gas chromatograph analysis was injected at 6 ml/hr into the top of the reactor under 2850 psi $H_2$ pressure. The internal temperature of the catalyst bed at the start of injection was adjusted to 97° C. by heating with a fluidized sand bath. The butadienepolyperoxide solution was allowed to trickle downward through the catalyst bed and withdrawn from the bottom of the reactor at the same rate as it was injected. An exothermic reaction which raised the internal temperature to 102° C., or 5° above the temperature of the sand bath, was noted. The effluent was assayed by gas chromatography, relating the amount of each product to the known quantity of 1,6-hexanediol present. After seven reactor volumes had been added and withdrawn, a steady state was reached. The yields of the various products were:

48.24%—1-butene-3,4-diol
30.28%—2-butene-1,4-diol
2.64%—4-hydroxybutyraldehyde
1.49%—2-hydroxybuten-3-aldehyde and hydroxymethyl vinyl ketone The products are over 99% unsaturated.

EXAMPLE 2

The apparatus described in Example 1 was charged with 1.2 g of a Ag-on-SiO$_2$ fibers catalyst prepared as in Example 1 but containing only 1% by weight Ag. The catalyst was reduced by heating for one hour at 2500 psi H$_2$ pressure at 226° C. A 10% by weight solution of butanedienepolyperoxide in tetrahydrofuran, containing a known amount of 1,6-hexanediol as a standard, was injected and withdrawn at 8 ml/hr with the reactor temperature at 100° and a hydrogen pressure of 2700–3000 psi. After 1.5hrs, the effluent analyzed for a yield of:
47%—1-butene-3,4-diol
25.88%—2-butene-1,4-diol
1.7%—2-hydroxybuten-3-aldehyde and hydroxymethyl vinyl ketone
0.8%—4-hydroxybutyraldehyde

EXAMPLE 3 BEST MODE

A Hastelloy C pressure vessel of 300 ml volume was reduced to a volume of 115 ml by insertion of a sleeve, which was then packed with 49 g of a 10% Ag-on-SiO$_2$ catalyst prepared as in Example 1 and 245 g of stainless steel shot. The reactor was run as a trickle-bed with a diffuser plate at the top to spread the liquid uniformly over the catalyst bed. A sump at the bottom of the reactor was drained by a dip tube. The injection and withdrawal rates were matched to keep a constant volume of liquid in the reactor. A methylacetate solution containing 10% by weight butadienepolyperoxide and 1.79% by weight of 1,6-hexanediol standard was injected and withdrawn at 100 ml/hr at a reactor temperature of 95° C. and a hydrogen pressure of 2300 psi. The effluent contained a yield of
41.15%—1-butene-3,4-diol
26.1%—2-butene-1,4-diol
5.09%—hydroxymethyl vinyl ketone and 2-hydroxybuten-3-aldehyde
4.16%—4-hydroxybutyraldehyde
0.44%—1,4-butanediol

EXAMPLE 4

A solution containing 5% by weight of butadienepolyperoxide plus a known amount of 1,6-hexanediol as a standard in a 50/50 by weight mixture of tetrahydrofuran and toluene was injected at 180 ml/hr into the apparatus of Example 3 packed with 35 g of 8.35% Ag-on-SiO$_2$ fibers. The reactor temperature was 95° and the H$_2$ pressure 2400 psi. The product contained:
54%—1-butene-3,4-diol
26%—2-butene-1,4-diol
<1%—1,2-butanediol
minor amounts—2-hydroxybuten-3-aldehyde hydroxymethyl vinyl ketone 4-hydroxybutyraldehyde

EXAMPLE 5

A 300 ml stirred Hastelloy C autoclave was charged with 50 g of a 10% Ag-on-SiO$_2$ fiber catalyst and a 10% solution of butadienepolyperoxide in tetrahydrofuran pumped in at 100 ml/hr at 95° and 2300 psi H$_2$ pressure. The residence time in the reactor was 55 min. The effluent contained a yield of:
41.06%—1-butene-3,4-diol
22.39%—2-butene-1,4-diol
4.5%—4-hydroxybutyraldehyde
4.29%—hydroxymethyl vinyl ketone and 2-hydroxybuten-3-aldehyde
3.075%—1,2-butanediol
6.30%—1,4-butanediol
15.3%—Unidentified byproducts

EXAMPLE 6

The apparatus of Example 1 was charged with 2.5 g of a 6.14% Ag-on-SiO$_2$ catalyst prepared as in Example 1 but using commercially available, high surface area silica gel granules as a support. A 10% solution of butadienepolyperoxide in tetrahydrofuran, to which 3.26% by weight 1,4-hexanediol reference standard had been added, was injected at 95° C. at 2 ml/hr at a H$_2$ pressure of 2900–3000 psi and withdrawn at the same rate. The product contained:
46.7%—1-butene-3,4-diol
20.4%—2-butene-1,4-diol
1.7%—4-hydroxybutyraldehyde
4.2%—2-hydroxybuten-3-aldehyde and hydroxymethyl vinyl ketone
3.075%—1,2-butanediol
6.30%—1,4-butanediol
15.3%—Unidentified byproducts

EXAMPLE 7

The apparatus of Example 1 was charged with 0.9 g of a 10% Ag-on-SiO$_2$ fiber which had been reduced by washing with an excess of sodium borohydride in water, then with water until washings were neutral, and finally tetrahydrofuran. A 10% solution of butadienepolyperoxide in tetrahydrofuran, which also contained 1,6-hexanediol as a reference standard, was injected at 89° C. at 2 ml/hr and 3000 psi H$_2$ pressure and withdrawn at the same rate. The product contained:
41.33%—1-butene-3,4-diol
29.38%—2-butene-1,4-diol
10.64%—1,4-butanediol
0.37%—1,2-butanediol

EXAMPLE 8

The reactor of Example 1 was charged with 1.6 g of a 10% Ag-on-coconut charcoal catalyst and the reduction run at 95° and 2500 psi H$_2$ injecting a 10% solution of butadienepolyperoxide in tetrahydrofuran plus a 1,6-hexanediol standard at 5 ml/hr. After reaching steady-state conditions, the product contained only traces of saturated diols and was a mixture of 1-butene-3,4-diol and 2-butene-1,4-diol and unsaturated aldehydes and ketone.

EXAMPLE 9

2-Butene-1,4-diol was separated by distillation from 1-butene-3,4-diol and other products prepared by the process described in Example 3. A solution of 0.92779 g 2-butene-1,4-diol with 0.22409 g 1,6-hexanediol standard in 9 g tetrahydrofuran was prepared. The solution was injected at 2800 psi and 150° C. at 2 ml/hr into a reactor similar to that described in Example 1 charged with 1.6 g of a 10% Ag-on-SiO$_2$ fiber catalyst prepared as in Example 1 and withdrawn at the same rate. After a total of 9 ml of the solution was pumped through the system (approximately 4.5 hrs), 0.282 g of 1,4- butanediol was recovered. Essentially all of the 2-butene-1,4-diol had been converted to the 1,4-butanediol.

EXAMPLE 10

The apparatus of Example 1 was charged with 6.5 g freshly precipitated, washed and dried silver oxide. The catalyst was reduced by heating at 150° C. and 2000 psi H$_2$ for 2 hrs. The reactor was then cooled to 95° C. and a 10% solution of butadienetetrahydrofuran plus tetraglyme as a standard was injected at 2 ml/hr at 2300 psi H$_2$ pressure. When equilibrium was reached, the product contained a yield of:

47.5%—1-butene-3,4-diol
26.5%—2-butene-1,4-diol
2.8%—4-hydroxybutyraldehyde
0.15%—1,4-butanediol
0.08%—1,2-butanediol

I claim:

1. A process for hydrogenating butadienepolyperoxide which comprises hydrogenating 1–20% by weight of butadienepolyperoxide in a solvent which is stable under the reaction conditions in the presence of hydrogen and a catalyst consisting essentially of at least 0.1% by weight of metallic silver at a temperature of from 75°–110° C. and a pressure of at least 2000 psia to form a reaction product containing 1-butene-3,4-diol and 2-butene-1,4-diol the improvement wherein the 2-butene-1,4-diol is separated from 1-butene-3,4-diol in the reaction product and contacted with hydrogen in the presence of a hydrogenation catalyst under hydrogenation condition to produce 1,4-butanediol and the 1-butene-3,4-diol is contacted with a soluble mercury salt in a hydroxylic solvent at temperatures of 20°–110° C. to produce 2,5-dihydrofuran.

2. A process for hydrogenating butadienepolyperoxide which comprises hydrogenating 1–20% by weight of butadienepolyperoxide in a solvent which is stable under the reaction conditions in the presence of hydrogen and a catalyst consisting essentially of at least 0.1% by weight of metallic silver at a temperature of from 75°–110° C. and a pressure of at least 2000 psia to form a reaction product containing 1-butene-3,4-diol and 2-butene-1,4-diol the improvement wherein the 2-butene-1,4-diol is separated from 1-butene-3,4-diol in the reaction product and the 1-butene-3,4-diol is contacted with a soluble mercury salt in a hydroxylic solvent at temperatures of 20°–110° C. to produce 2,5-dihydrofuran.

* * * * *